United States Patent
Marians et al.

(10) Patent No.: US 6,699,693 B1
(45) Date of Patent: Mar. 2, 2004

(54) PROCESS FOR DNA REPLICATION

(75) Inventors: Kenneth Marians, New York, NY (US); Joing Liu, Shanghai (CN)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/890,829

(22) PCT Filed: Feb. 3, 2000

(86) PCT No.: PCT/US00/04445

§ 371 (c)(1),
(2), (4) Date: Oct. 26, 2001

(87) PCT Pub. No.: WO00/46408

PCT Pub. Date: Aug. 10, 2000

Related U.S. Application Data

(60) Provisional application No. 60/118,703, filed on Feb. 4, 1999.

(51) Int. Cl.⁷ .......................... C12P 19/34; C12Q 1/68; C07H 21/02; C07H 21/04; C07H 21/00
(52) U.S. Cl. ...................... 435/91.2; 435/6; 435/91.1; 536/23.1; 536/24.3; 536/24.33; 536/25.3; 536/25.32
(58) Field of Search .................. 435/6, 7.32, 91.1, 435/91.2, 183; 436/94; 536/23.1, 23.7, 23.72, 24.3, 24.33, 25.3, 25.32

(56) References Cited

U.S. PATENT DOCUMENTS 5,583,026 A    12/1996  O'Donnell
5,668,004 A     9/1997  O'Donnell

OTHER PUBLICATIONS

Janniere, et al., Replication terminus for DNA polymerase I during initiation of pAMbetal replication: role of theplasmid–encoded resolution system. Molecular microbiology. 1997, vol. 23, No. 3, 525–535, especially pp. 525–527 and 533.

McGlynn et al. The DNA replication protein PriA and the recombination protein RecG biad D–loops. J. Mol. Biol. q1997, vol. 270, pp. 212–221, especially pp. 212–214 and 217–220.

Karet et al. Quantification of mRNA in human tissue using fluorescent nested reverse–transcriptase polymerase chain reaction. Anal. Biochem. 1994, vol. 220, pp. 384–390, especially pp. 385 and 386.

Masai, et al. *Escherichia coli* PriA protein is essential for inducible and constitutive stable DNA replication, EMBO J. 1994, vol. 13, No. 22, pp. 5338–5345, especially pp. 5338, 5339, 5344 and 5345.

(List continued on next page.)

*Primary Examiner*—Ethan Whisenant
*Assistant Examiner*—Frank W Lu
(74) *Attorney, Agent, or Firm*—Oppedahl & Larson LLP

(57) ABSTRACT

A method is provided for replicating DNA, and in particular for replicating large segments of DNA. A primer is combined with a target DNA molecule to be replicated. The primer is designed to be at least partially homologous to a known site on the target DNA, and to create a D-loop when hybridized with that site. A replisome is then assembled at the D-loop, and this replisome creates a copy of the DNA, starting at the primer binding site. By utilizing two species of D-loop primers which bind to remote sites on the DNA flanking a region to be replicated, large sections of DNA can be replicated in a manner comparable to PCR. The replicated DNA can be analyzed to detect variations in the genetic sequence of the target, for linkage mapping and as a source of longer DNA molecules having a desired sequence.

11 Claims, 1 Drawing Sheet

OTHER PUBLICATIONS

Al–Deib et al. Modulation of recombination and DNA repair by the reeG and PriA helicases of *Escherchia cili* K–12. J. Bacteriol. Dec. 1996, vol. 178, No. 23, pp. 6782–6789, see entire document.

Marians, At the Crossroads between DNA Replication and Recombination, Ray Wu Symposium, Aug. 15, 1998.

Marians, et al., Pria and the Intersection between DNA Replication and Recombination.

Seufert, et al., Initiation of *Escherichia coli* minichromosome replication at oriC and at protein n' recognition sites. Two modes for initiating DNA synthesis in vitro. The EMBO Journal vol. 5, No 12, pp. 3401–3406, 1986.

Jones, et al., The ΦX174–type primosome promotes replisome assembly at the site of recombination in bacteriophage Mu transposition, The EMBO Journal vol. 16 No. 22, pp. 6886–6895, 1997.

Asai, et al, D–Loops and R–Loops: Alaternative Mechanisms for the initiation of Chromosome Replication in *Escherichia coli*, Journal of Bacteriology, Apr. 1994, pp. 1807–1812, vol. 176, No. 7.

Devlin, Textbook of Biochemistry with Clinical Correlations, $3^{rd}$ Ed., 1992.

US 6,699,693 B1

PROCESS FOR DNA REPLICATION

This application is a §371 national stage application of International Patent Application No. PCT/US00/04445 filed Feb. 3, 2000, and claims the benefit of U.S. Provisional Application No. 60/118,703 filed Feb. 4, 1999.

This application claims priority from U.S. Provisional Application No. 60/118,703, which application is incorporated herein by reference for those countries where such incorporation is allowed.

This application was supported by NIH Grant No. GM34557. The United States may have rights under this application.

BACKGROUND OF THE INVENTION

This application relates to a process for DNA replication, and to the application of this process for a variety of purposes.

Replication of DNA and other nucleic acids is a complex natural phenomenon which occurs within all biological systems. To facilitate the exploitation of the resources represented in the diverse genetic materials of the world's organisms, however, it is desirable to be able to replicate selected DNA sequences under more controlled conditions, for example to produce increased amounts of one sequence. Such replication of selected DNA sequences is required for a great many applications of potential scientific and industrial significance, and has been accomplished by a variety of techniques. These include cloning of the DNA sequences into plasmids or genes, and replication of the plasmid using the DNA replication mechanisms of a host organism, and amplification techniques such as PCR or ligase amplification. Cloning is capable of replicating complete gene sequences, but requires the introduction of the sequences into a host organism, and the subsequent recovery of the duplicated DNA. PCR and similar amplification techniques offer increased flexibility, including the ability to introduce labels and/or sequence variations into the replicated DNA, and avoid the use of a host organism, but are limited in the length of the sequence which can be replicated. Thus, there remains a need for a methodology which will permit the replication of long DNA molecules, while providing the flexibility associated with PCR amplification. It is an object of the present invention to provide such a methodology.

SUMMARY OF THE INVENTION

The present invention provides a method for replicating DNA, and in particular for replicating large segments of DNA. In accordance with the invention, a primer is combined with a target DNA molecule to be replicated. The primer is designed to be at least partially homologous to a known site on the target DNA, and to create a D-loop when hybridized with that site. A replisome is then assembled at the D-loop, and this replisome creates a copy of the DNA, starting at the primer binding site. By utilizing two species of D-loop primers which bind to remote sites on the DNA flanking a region to be replicated, large sections of DNA can be replicated in a manner comparable to PCR.

The replicated DNA can be analyzed to detect variations in the genetic sequence of the target, for linkage mapping and as a source of longer DNA molecules having a desired sequence.

DETAILED DESCRIPTION OF THE INVENTION

Figure 1:
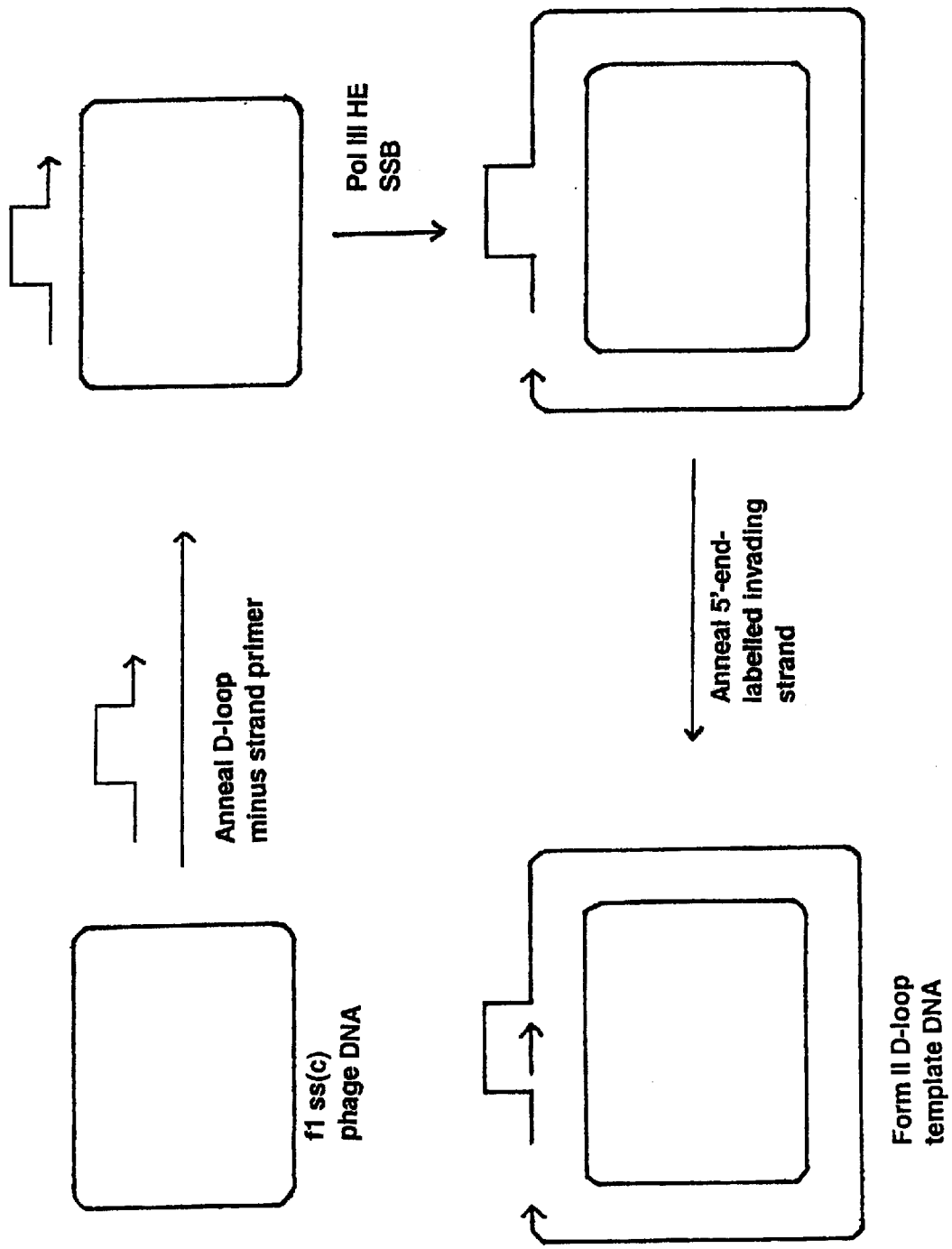
FIG. 1 shows the scheme used for making a double-stranded circular template DNA molecule containing a D-loop, which was used to validate the concept of the invention.

The present invention provides a method for the controlled replication, generally in vitro, of selected regions of DNA. In accordance with the invention, replication of a target region of a target DNA molecule is accomplished by:

(a) introducing a D-loop into the target DNA molecule at a selected initiation point adjacent to the target region;

(b) assembling a replisome at the D-loop; and (c) providing DNA monomers (dNTPs) and ATP, whereby the target region is replicated. ATP is preferably provided at concentrations in excess of about 1 mM. ATP is required because the formation of a processive DNA polymerase complex requires ATP hydrolysis and also because DnaB, the DNA helicase, requires concentration in excess of 1 mM to be maximally active.

Introduction of a D-loop at a selected initiation site in duplex DNA can be accomplished using an oligonucleotide primer which hybridizes with double-stranded DNA at a selected initiation site. The non-hybridized strand is displaced to create the D-loop. D-loop formation can be driven by the homologous pairing enzyme, RecA, as has been described in the literature. See, McEntee et al., *Proc. Nat'l Acad. Sci. (USA)* 76: 2615–2619 (1979), which is incorporated herein by reference. D-loop formation could also be driven by other methods, for example heating at a moderately high temperature (for example 75–80° C.) may be enough to drive annealing, particularly in regions rich in A+T bases.

The oligonucleotide primer which is used for generation of the D-loop generally has a length of from 20 to about 50 bases. The primer is selected to be substantially complementary to one of the two strands of the target DNA duplex at the initiation site. As used herein, the term "substantially complementary" refers to a primer which will hybridize with the target DNA duplex under conditions of moderately high stringency. However, it will be appreciated that RecA mediated hybridization, if employed, is an enzymatic strand-pairing reaction, and that conditions normally used for DNA-DNA hybridization (e.g. 0.6 M NaCl) would actually be inhibitory. Thus the precise conditions corresponding to "moderately high stringency" may vary depending on the methodology used to drive the annealing. In a general sense, however, the term "substantially complementary" includes (1) primers which are perfectly complementary to the target DNA molecule, (2) primers which are complementary for most of their length, but which include one or several mismatches from perfect complementarity, although not enough mismatches to significantly reduce hybridization specificity; and (3) degenerate primers which include several bases at a given site to accommodate a multiplicity of common alleles in the target DNA. The use of mismatched primers may result from the presence of a mutation in the initiation site, or the mismatch may be intentionally selected for introduction of a desired sequence variation into the replicated DNA.

The primers used in the invention may also include one or more non-hybridized regions for the purpose of introducing a desired additional sequence into the replicated DNA. For example, this additional sequence may be a sequence which introduces a restriction site near the end of the replicated DNA to facilitate insertion of the replicated copies into other DNA molecules. Preferred restriction sites will be those recognized by rare-cutting restriction enzymes which generally recognize 8-base sequences, or intron-homing endonucleases such as PI-SceI from yeast which recognizes a 31-base pair sequence. This will reduce the likelihood of cleavage occurring within the replicated DNA at other than the intended cleavage site.

In an alternative embodiment of the invention useful with single-stranded templates, the primer used comprises a 3'- and a 5' region which are substantially complementary to portions of the target DNA template, and a central non-complementary region which forms a D-loop when the primer is hybridized with the target DNA. A second primer which is complementary is used to form the invading strand of the D-loop. Similar variations for insertion of cleavage sites etc, may be incorporated in the structure of such primers.

The primers used in the method of the invention may also include a detectable label or capture moiety. Suitable detectable labels and capture moieties are well known in the art as comparable materials are used in PCR, nucleic acid sequencing, and hybridization-based assays. Specific, non-limiting examples of suitable labels and/or capture moieties include fluorescent dyes such as fluorescein, Texas Red or cyanine dyes; enzyme labels such as alkaline phosphatase; and capturable labels such as biotin. Nucleic acid tails which specifically interact with a known capture sequence can also be employed.

In a preferred embodiment of the invention, the primer is combined with target double-stranded DNA under conditions suitable for hybridization and in the presence of the enzyme RecA, which results in the formation of a D-loop at the site of primer binding. Unlike common in vitro processes such as PCR, which utilize bacterial polymerases of inherently low processivity, the present invention utilizes replisome. Replisomes are multi-protein associations which form at a replication fork and act in concert to replicate DNA. Replisomes provide much greater processivity than polymerases used for PCR. For example, the $E.$ $coli$ replisome can synthesize pieces of DNA at least as long as a megabase ($1 \times 10^6$ nucleotides). The fidelity of copying is also quite high, with the $E.$ $coli$ replisome making fewer than 1 mistake in $10^8$ nucleotides synthesized. Furthermore, unlike PCR, replisomes are substantially insensitive to regions of secondary structure in the DNA template. Thus, utilization of replisomes offers numerous advantages over the use of polymerases.

Replisomes include proteins which perform a variety of functions. Replication of DNA using replisomes depends on an initial unwinding of the DNA duplex at an origin of replication, and the continued unwinding along the strands as the replication process proceeds. This unwinding is carried out by DNA helicases. The resultant regions of single-stranded DNA are stabilized by the binding of single-stranded DNA-binding proteins which are also part of the replisome. The stabilized single-stranded regions are then accessible to the enzymatic activities of polymerases enzymes required for replication to proceed.

Replisomes have been shown to be substantially self assembling. Thus, when the necessary proteins are present under appropriate conditions, the replisome will assemble. We have found that this assembly will occur at a D-loop. A preferred combination of a proteins for formation of a replisome in accordance with the present invention includes the following proteins:

PriA, PriB, PriC, DnaT, DnaB, DnaC (primosomal proteins);
single-stranded DNA-binding protein (SSB); and
DNA polymerase III holoenzyme (Pol III HE).

An alternative combination utilizes the mutant protein DnaC810, (described below) in place of PriA, PriB, PriC and DnaT.

The preparation and recovery of these various proteins is well described in the art, including the art cited below which is incorporated herein by reference. Pol III HE may be used in a form recovered directly by purification from $E.$ $coli$, or as a combination of Pol III* and the β subunit. Pol III HE may also be reconstituted from individually overexpressed and purified subunits. These subunits are α (DnaE), ε (DnaQ), θ (HolE), β (DnaN), τ (DnaX, full length), γ (DnaX, truncated), δ (HolA), δ' (HolB), χ (HolC) and ψ (HolD). Preparation of Pol III HE is described in U.S. Pat. Nos. 5,668,004 and 5,583,026 which are incorporated herein by reference for those countries in which such incorporation is permitted.

Replisomes have been found to initiate DNA replication at the site of a D-loop. Thus, the D-loop formed by the interaction of the primer with the target DNA molecule serves as the initiation site for the replication process in accordance with the invention. When appropriate nucleic acid monomers (i.e., deoxynucleotide triphosphates, dATP, dCTP, dGTP and dTTP) and ATP are available, a copy of the strand of the DNA molecule to which the primer hybridizes is produced. The length of replicated material which can be produced in this way is much greater than the length which can be produced using PCR or comparable techniques, with lengths in excess of 5000–500,000 bases being readily attainable. Thus, the method provides the ability to make copies of entire large genes, including both intron and exon sequences.

As will be apparent to persons skilled in the art, a person making copies of DNA will generally be interested in obtaining those copies of a particular region of the DNA, which is referred to herein as the "target region." The target region may be a particular gene, or a particular portion of a gene depending on the use for which the copied DNA is intended. The ability to produce copies of very large numbers of bases changes the practical limits on the proximity between the primer and the target region from those which are usually observed in the PCR and comparable methods. Thus, while the initiation site must be "adjacent" to the target region, this means only that the initiation site must be close enough to and on the correct side of the target region such that a replisome assembled at the D-loop will copy the DNA of the target region.

In a preferred embodiment of the invention, two primers are utilized. The first primer is as described above, and hybridizes with a first strand of a double stranded DNA duplex. The second primer also is a substantially complementary oligonucleotide primer, but it hybridizes to the second strand of the DNA duplex at a second initiation site located on the other side of the target region. Thus, the two primers flank the target region, in the same manner that PCR primers flank a region to be amplified. Further, the same principle which leads to amplification of just the region bounded by PCR primers, leads to creation of much larger pieces of replicated DNA spanning the region between the two initiation sites using the method of the invention, although the efficiency may not be as great as achieved with PCR. This reduced efficiency is less of a problem than one might expect, however, since the large size of the replicated DNA makes them inherently more detectable than small fragments. On the other hand, since the process of the invention works on double-stranded DNA, it is not necessary to separate the strands of the target and the newly replicated DNA before proceeding with the next cycle.

While the large size of the replicated DNA offers advantages for purposes of detection, it may also pose problems. Very large DNA molecules (i.e., those that are hundred of kilobases in length) are fragile, and nay be broken if manipulated in simple solutions. Thus, production of fragments of such lengths, and meaningful analysis of the lengths of such fragments may require that the reaction be performed in a supporting matrix, such as an agarose gel. Replicated DNA can be transferred out of the supporting matrix, for example for introduction into a matrix for separation based on size by electrophoresis.

DNA replicated in accordance with the invention may be utilized for a variety of purposes. First, the replicated DNA may be used as a source of genetic material to be spliced into still larger nucleic acid constructs, including plasmids, cosmids, viral vectors etc., to facilitate expression of the replicated DNA in a suitable host system. Such splicing can be facilitated by the incorporation of restriction sites near then ends of the replicated DNA as discussed above. When two primers are utilized, restriction sites can be introduced at both ends of the replicated DNA.

Second, the replication of DNA in accordance with this method can be used as part of a method for detecting genomic rearrangements in a target DNA sequence. In such a method, a D-loop is introduced into the DNA at a selected initiation point, a replisome is assembled at the D-loop, and the DNA is copied to produce sufficient numbers of copies for analysis. The copied product is analyzed to detect variations in size or organization of the copied material using size-specific separations, hybridization probes and other standard analytical techniques. It will be appreciated that the use of size-specific separations requires the production of a product of defined lengths, and thus will generally require the use of the two primer embodiment discussed above. On the other hand, where the analysis involves the measurement of the interaction of the DNA with a labeled or immobilized probe, the replication of multiple copies of a single strand of the DNA, without amplification, may be sufficient.

Third, the method can be used to facilitate linkage mapping. For example, the method can be used in the circumstance where two chromosomal markers are known to be near one another, but where the exact distance separating them is not known. D-loop oligonucleotide primers are synthesized for each marker for both the DNA strands. Combinations of the pruners are used to replicate the region between the two markers, and the size of the product formed reflects the chromosomal distance between the two markers. The method may also be used to map unlinked genes, and markers such as RFLPs, SNIPs and ESTs.

To demonstrate the ability of the replisomes to assemble at a D loop and replicate the DNA, we used a small bacteriophage DNA molecule as a model system as described in the following non-limiting examples. The conditions for replisome assembly and DNA replication can be extended to use with larger molecules, and with substantially complementary primers as discussed above.

EXAMPLE 1

Preparation of DNA Replication Proteins

To prepare DnaC810, a dnaC810 open reading frame was constructed by splicing overlap extension polymerase chain reaction and cloned into the NdeI site of the pET11C overexpression plasmid (Novagen). Overexpression and purification of DnaC810 was as for the wild type protein.

PriA, PriB, PriC, DnaT, DnaB and DnaC were purified by the methods described in Marians, K. J. *Methods Enzymol.* 262: 507–521 (1995). SSB was purified using the procedures described in Minden and Marians, *J. Biol. Chem.* 260: 9316–9325 (1985). The DNA polymerase III holoenzyme was either reconstituted from Pol III* and β subunit as described by Wu et al. *J. Biol. Chem* 267: 4030–4044 (1992) or from purified subunits as described in Marians et al., *J. Biol. Chem.* 273: 2452–2457 (1998).

EXAMPLE 2

To validate the operability of the inventive concept, a double-stranded circular template DNA was prepared in accordance with the steps shown in FIG. 1. A 100 nt-long oligonucleotide primer (Seq. ID No. 1) was annealed to f1R408 viral DNA (Russell et al., *Gene* 45: 333–339 (1986)). The central 42 nt of this oligonucleotide are non-homnologous with the template, thus forming a D-loop in the resulting heteroduplex. Incubation of the heteroduplex with DNA Polymerase III holoenzyme in the presence of SSB and DNA monomers resulted in the extension of the primer and the formation of a nicked form II DNA with a 42 nt-long bubble region. During the last two minutes of this incubation, ddTTP and ddATP were introduced at concentrations 20-fold higher than dTTP and dATP to ensure that complementary strand synthesis could not be extended further. After phenol extraction and ethanol precipitation, the DNA products were purified by electrophoresis through native agarose gels. Complete form II bubble DNA was recovered from the gel and a $[5'-^{32}P]$ minus strand oligonucleotide (Seq. ID. No. 2) was then annealed to the D loop form II template. The template was then gel filtered through Biogel A5M to remove unannealed oligonucleotide and unincorporated $[\gamma-^{32}P]$ ATP.

EXAMPLE 3

Reaction mixtures (12 μl) containing 50 mM Hepes-KOH (pH 8.0), 10 mM MgOAc, 10 mM DTr, 80 mM KCL 200 μg/ml bovine serum albumin, 2 mM ATTP, 40 μM dNTPs, 0.42 nM $[^{32}P]$ form II D loop DNA template, 0.5 μM SSB, 225 nM DnaC, 30 nM DNA polymerase III holoenzyme, PriA, PriB, PriC, DnaT and DnaB were incubated at 37° C. for 10 minutes. To test the sufficiency of various combinations of proteins to replicate the template prepared in Example 2, reactions were also performed in which one of the proteins (PriA, PriB, PriC, DnaT, DnaC and DnaB) was omitted in each reaction mixture. As controls, template alone and template with the holoenzyme alone were also evaluated. Reactions were terminated by the addition of EDTA to a concentration of 25 mM and NaOH to a concentration of 50 mM. The reaction products were evaluated by electrophoresis at 2 V/cmn for 20 hours at room temperature through horizontal 0.7% alkaline agarose gels using 30 mM NaOH, 2 mM EDTA as the electrophoresis buffer. The gels were neutralized, dried and analyzed by autoradiography.

The electrophoresis gels showed that incubation of the D-loop template, the seven primosomal proteins, SSB and DNA polymerase III holoenzyme resulted in extension of the invading strand oligonuctetotide (42 nt, Seq. ID. No. 2) to the full length template size (6.4 kb). The efficiency of the reaction varied, but generally 15–30% of the invading strand could be elongated to full length in a 10 minute incubation. The reaction exhibited an absolute requirement for all of the primosomal proteins except PriC. Omission of this protein resulted in a decrease in DNA synthesis to one-third that of the complete reaction. This observation was similar to those reported for replication on different templates. Ng et al., *J. Biol. Chem.* 271: 15642–15648 (1996). Some extension of the invading strand by the holoenzyme alone could be observed, but this was suppressed by the presence of PriA.

If the invading strand was omitted from the reaction, and [α$^{32}$P] dATP was included, no DNA replication could be observed.

EXAMPLE 4

Because DNA helicases were being introduced to the DNA during primrose assembly, extension of the invading strand could result from one of two processes: either (1) assembly of a bona fide replication fork at the D loop followed by elongation of the leading strand coupled with unwinding of the duplex DNA template, or (2) uncoupled unwinding of the template DNA leaving an oligonucleotide annealed to the viral single stranded DNA that could be elongated in a primer extension reaction by the polymerase. We previously showed that coupled replication fork action requires a protein-protein interaction between DnaB and the τ subunit of the holoenzyme. Kim et al., *Cell* 84: 643–650 (1996). In the presence of this interaction, replication forks could move rapidly, at nearly 1000 nt/sec, whereas in its absence, the polymerase becomes stuck behind a slow-moving helicase and replication fork progression proceeds at only about 30 nt/sec.

To evaluate the mechanism active in the replication of DNA in the method of the invention, the speed of elongation of the invading strand was assessed in the presence and absence of τ using holoenzyme reconstituted from individual purified subunits. Ten second time points were taken from the start of the reaction, and the elongated products were examined on denaturing gels. Full length material could be observed in the presence of τ after 10 seconds, whereas even after 60 seconds no full length material was observed in its absence. This corresponds to a rate of replication fork progression in the presence of τ of 600–700 nt/sec, similar to what has been observed in the past for other replication systems.

Mok et al., *J. Biol. Chem.* 262: 16644–16654 (1987). Thus, we conclude that bona fide replication fork assembly occurs at the D loop on the template in the presence of primosomal proteins, SSB and the holoenzyme.

EXAMPLE 5

All of the phenotypes of priA null mutations can be suppressed by mutated priA alleles that encode PriA proteins that are no longer ATPases or DNA helicases, but still catalyze primosome assembly. Zavitz et al., *J. Biol. Chem* 267: 6933–6940 (1992). These mutations are substitutions in the invariant Lys in the Walker A box nucleotide-binding motif. If the PriA-dependent replication fork assembly described here were relevant to what happened in the cell, we would expect these mutant proteins to substitute fully for wild-type PriA in the replication reaction. To test this, three mutant proteins, having the K230R, K230A and K230D substitutions were tested. All three supported replication on the D loop to a greater extent than the wild-type protein. This same type of improved activity in the mutant proteins has been observed in other systems (Zavitz, supra), and may arise because the mutant proteins remain bound to the site of DNA binding, providing a better target than the wild-type protein that can move off the site because of its helicase activity.

EXAMPLE 6

*E. coli* strains carrying priA mutations are very difficult to grow. They are rich-media sensitive, form huge filaments, and have a viability roughly one-hundredth that of the wild-type. Sandler et al., *Genetics* 143: 5–13 (1996); Nurse et al., *J. Bacteriol.* 6686–6693 (1991); Masai et al., *EMBO J.* 13: 5338–5345 (1994). Suppressor mutations that restore viability, as well as ablate constitutive induction of the SOS response and the defects in homologous repair of UV-damaged DNA, arise overnight after transduction of the priA2:kan allele into fresh recipient cells. The mutations map to dnaC. (Sandier, supra). DnaC forms a complex with DnaB in solution (Wicker et al., *Proc. Natl. Acad Sci.* (*USA*) 72: 921–925 (1975), and is required for the efficient transfer of DnaB to DNA in the presence of other replication protein. Marians et al., *Ann. Rev. Biochem.* 61: 673–719 (1992). In order to assess the biochemical properties of these altered DnaC proteins, one such suppressor allele, dnaC810, was molecularly cloned into an expression plasmid and the mutant protein purified as described in Example 7, infra.

Strains carrying dnaC810 no longer require PriA for viability. This suggests that if the essential role for PriA in cellular metabolism was to catalyze assembly of replication forks at recombination intermediates, DnaC810 must be able to bypass the requirement for PriA to recognize the D loop and nucleate the assembly of a primosome. Accordingly, we tested whether DnaC810 alone could direct transfer of DnaB to the D loop template DNA.

In the presence of SSB and the holoenzyme, the combination of wild-type DnaC and DnaB did not support elongation of the invading strand of the D loop. On the other hand, DnaC810 was clearly able to load DnaB to the D loop on the template in the absence of the other primosomal proteins, as evidenced by the elongation of the invading strand to full length. Thus, the E176G substitution in DnaC810 represents a true gain of function mutation that allows bypass of the DnaB loading pathway that involves PriA, PriB, PriC and DnaT and permits a reduction in the number of proteins necessary for the practice of the present invention.

Interestingly, the relative efficiencies of the replication reaction catalyzed in the presence of DnaC810 and DnaB varied compared to the reaction catalyzed by the complete set of primosomal proteins. At 80 mM KCl, the DnaC810 reaction was 5- to 10-fold more efficient. However, at 600 mM potassium glutamate, the reaction catalyzed by the complete set of proteins was more efficient by a factor of 2. While not intending to be bound by a particular mechanism, this difference may arise from differences in the relative stability of intermediate complexes that are formed during the loading of DnaB to DNA.

EXAMPLE 7

Construction of Plasmid pET11c-dnaC810

A dnaC810 open reading frame (ORF) was made by two-step overlapping polymerase chain reaction (PCR) Morton et al., *Gene* 77: 61–68 (1989). The N-terminal coding region of dnaC810 was PCR amplified using plasmid pE11c-dnaC (Marians, K. J, *Methods Enzynol.* 262:m 507–521 (1995)) as a template and two flanking primers:
  (i) the NdeI primer (Seq. ID No. 3), which carries a NdeI site at the dnaC initiator codon, and
  (ii) the AgeI' primer (Seq. ID. No. 4), which carries the designed point mutation (E176G, GAA-GGT). The C-terminal coding region of dnaC810 was also PCR amplified using plasmid pET11c-dnaC as a template and two different flanking primers:
  (i) the AgeI primer (Seq. ID No. 5), which is complementary to the AgeI' primer and
  (ii) the BamHI primer (Seq. ID No. 6), which carries a BamHI site just downstream of the dnaC stop codon.

These overlapping N- and C-terminal fragments were gel purified after PCR and further PCR extended and amplified with the two flanking NdeI and BamHI primers. The gel purified dnaC810 ORF fragment was digested with NedI and BamHI and ligated with NedI- and BamHl-digested pET11c plasmid DNA to give pET11 c-dnaC810.

Purification of DnaC810

Because of the extreme overproduction, DnaC810 was followed during purification by SDS-PAGE. BL21(DE3) pLysS carrying pET11c-dnaC810 was grown in 12 1 L Broth (Mainatis et al., *Molecular Cloning: A Laboratory Manual*, Cold Spring Harbor Laboratory Press, Cold Spring Harbor, N.Y. (1982)) containing 0.4% glucose and 300 mg/ml ampicillin to $OD_{600}$=0.4 and then induced in the presence of 1 mM IPTG for 3 h. Cells were chilled, pelleted by centrifugation, and resuspended in 50 mM Tris-HCl (pH 8.4 at 4° C.) and 10% sucrose. The cell suspension (50 ml) was adjusted to 150 mM KCl, 20 mM EDTA, 5 mM dithiothreitol, 0.02% lysozyme, and 0.1% Brij 58 and incubated at 0° C. for 10 min. This suspension was centrifuged at 100,000×g for 1 h (Sorvall T865 rotor). The supernatant (fraction 1, 65 ml, 3510 mg protein) was adjusted to 0.04% polymin P by dropwise addition of a 1% solution. The precipitate was removed by centrifugation at 47,000×g in a Sorvall SS-34 rotor for 30 min. The supernatant was further subjected to $(NH_4)_2SO_4$ fractionation (50% saturation) by the addition of solid. The resulting protein pellet was collected by centrifugation at 47,000×g in a Sorvall SS-34 rotor for 30 min. The protein pellet was resuspended in 8 ml of buffer A [50 mM Tris-HCl (pH 7.5 at 4° C.), 1 mM EDTA, 5 mM dithiothreitol, 20% glycerol, 0.01% Brij 58] +50 mM NaCl to give fraction 2 (13 ml, 1108 mg protein). Fraction 2 was dialyzed against 21 of buffer A+50 mM NaCl for 12 h and then loaded onto a 100-ml DEAE-cellulose column (4 cm×20 cm) that had been equilibrated previously with buffer A+50 mM NaCl. The column was washed with 200 ml of buffer A+50 mM NaCl. Fractions (15 ml) of the flow-through and wash that contained protein were pooled to give fraction 3 (81 ml, 363 mg protein). Fraction 3 was loaded directly onto a 35-ml SP-Sepharose FF column (formed in a 60-ml disposable syringe) that had been equilibrated previously with buffer A+50 mM NaCl. The column was washed with 200 ml of buffer A+50 mM NaCl and protein was then eluted with a 350-ml linear gradient of 50–300 mM NaCl in buffer A. DnaC810 eluted at 175 mM NaCl (fraction 4, 24 ml, 25 mg protein). Fraction 4 was then loaded directly onto a 6-ml hydroxylapatite column (packed in a 10-ml disposable syringe) that had been equilibrated previously with buffer A+200 mM NaCl. The column was washed with 12 ml of equilibration buffer and protein was eluted with a 60-ml linear gradient of 0–400 mM $(NH_4)_2SO_4$ in buffer A+200 mM NaCl. DnaC810 eluted at 150 mM $(NH_4)_2SO_4$ to give fraction 5 (5.2 ml, 16.5 mg protein). Fraction 5 was concentrated bydialyzing against buffer A+50 mM NaCl+ 30% polyethylene glycol 20,000 and loaded onto a 125-ml Superdex-200 FPLC column that had been equilibrated with buffer A+50 mM NaCl. The column was eluted at 1 ml/min. Fractions (1 ml) containing DnaC810 were pooled to give fraction 6 (7.5 ml, 9.2 mg protein). Fraction 6 was then loaded onto a 3-ml phosphocellulose column that had been equilibrated with buffer A+50 mM NaCl. The column was washed with 6 ml of equilibration buffer and protein was eluted with a 60-ml linear gradient of 50–400 mM NaCl in buffer A. DnaC810 eluted at 250 mM NaCl (Fraction 7, 3.5 ml, 5.2 mg protein).

What is claimed is:

1. A method for replication of a target region of a target DNA molecule comprising the steps of:
   (a) introducing a D-Loop into the target duplex DNA molecule at a first initiation point adjacent to the target region in a reaction mixture, wherein the step of introducing a D-loop is performed by hybridizing the duplex DNA molecule with a first oligonucleotide primer which is substantially complementary to the first initiation site;
   (b) adding proteins to the reaction mixture to assemble a replisome at the D-loop; and
   (c) providing DNA monomers and ATP to the replisome, whereby the target region is reproduced, and further comprising the step of introducing a second D-loop by hybridizing the duplex DNA molecule with a second oligonucleotide primer which is substantially complementary to a second initiation site, said target region lying between the first and second initiation sites.

2. The method of claim 1, wherein the first oligonucleotide primer has a length of from 20 to 50 bases.

3. The method of claim 1, wherein the first oligonucleotide primer comprises a detectable label or capture moiety.

4. The method of claim 1, wherein the first and second oligonucleotide primers each have a length of from 20 to 50 bases.

5. The method of claim 1, wherein at least one of the oligonucleotide primers comprises a detectable label or capture moiety.

6. The method of claim 1, wherein the replication is performed in a supporting matrix.

7. The method of claim 1, wherein the replisome is assembled via the action of primosomal proteins, single-stranded DNA-binding protein and the DNA polymerase III holoenzyme.

8. The method of claim 7, wherein the primosomal proteins includes a mutant PriA protein which lacks ATPase and helicase functionality.

9. The method of claim 3, wherein the replication is performed in a supporting matrix.

10. The method of claim 3, wherein the replisome is assembled via the action of primosomal proteins, single-strand binding protein and holoenzyme III.

11. The method of claim 10, wherein the primosomal proteins includes a mutant PriA protein which lacks ATPase and helicase functionality.

* * * * *

SEQUENCE LISTING

```
<160> NUMBER OF SEQ ID NOS: 6

<210> SEQ ID NO 1
<211> LENGTH: 100
<212> TYPE: DNA
<213> ORGANISM: Escherichia coli
<220> FEATURE:
<223> OTHER INFORMATION: primer

<400> SEQUENCE: 1
acatacataa aggtggcaac gccattcgaa atgagctcca tatgctagct agggaggccc      60
ccgtcacaat caatagaaaa ttcatatggt ttaccagcgc                          100

<210> SEQ ID NO 2
<211> LENGTH: 42
<212> TYPE: DNA
<213> ORGANISM: Escherichia coli
<220> FEATURE:
<223> OTHER INFORMATION: minus strand oligonucleotide

<400> SEQUENCE: 2
atataaaaga aacgcaaaga caccacggaa taagtttatt tt                        42

<210> SEQ ID NO 3
<211> LENGTH: 34
<212> TYPE: DNA
<213> ORGANISM: Escherichia coli
```

-continued

```
<220> FEATURE:
<223> OTHER INFORMATION: NdeI primer

<400> SEQUENCE: 3
taatgcaggc catatgaaaa acgttggcga cctg                    34

<210> SEQ ID NO 4
<211> LENGTH: 24
<212> TYPE: DNA
<213> ORGANISM: Escherichia coli
<220> FEATURE:
<223> OTHER INFORMATION: AgeI' primer

<400> SEQUENCE: 4
tcgtatttcg aaccggtctg cacg                               24

<210> SEQ ID NO 5
<211> LENGTH: 24
<212> TYPE: DNA
<213> ORGANISM: Escherichia coli
<220> FEATURE:
<223> OTHER INFORMATION: AgeI primer

<400> SEQUENCE: 5
cgtgcagacc ggttcgaaat acga                               24

<210> SEQ ID NO 6
<211> LENGTH: 37
<212> TYPE: DNA
<213> ORGANISM: Escherichia coli
<220> FEATURE:
<223> OTHER INFORMATION: BamHI primer

<400> SEQUENCE: 6
ttaagcactg ggatccttaa tactctttac ctgttac                 37
```